US00PP28278P3

(12) United States Plant Patent
Elsinga

(10) Patent No.: US PP28,278 P3
(45) Date of Patent: Aug. 15, 2017

(54) ***MANDEVILLA* PLANT NAMED 'FRI0613'**

(50) Latin Name: ***Mandevilla* hybrid**
Varietal Denomination: FRI0613

(71) Applicant: Sietse Elsinga, Beamsville (CA)

(72) Inventor: Sietse Elsinga, Beamsville (CA)

( * ) Notice: Subject to any disclaimer, the term of this patent is extended or adjusted under 35 U.S.C. 154(b) by 167 days.

(21) Appl. No.: 14/756,139

(22) Filed: Aug. 5, 2015

(65) Prior Publication Data

US 2016/0120087 P1 Apr. 28, 2016

(30) Foreign Application Priority Data

Oct. 23, 2014 (CA) ..... PBR 14-8460

(51) Int. Cl.
*A01H 5/02* (2006.01)

(52) U.S. Cl.
USPC ..... Plt./232

(58) Field of Classification Search
USPC ..... Plt./226, 232
See application file for complete search history.

*Primary Examiner* — Susan McCormick Ewoldt
*Assistant Examiner* — Karen Redden
(74) *Attorney, Agent, or Firm* — Penny J. Aguirre

(57) ABSTRACT

A new cultivar of *Mandevilla* plant named, 'FRI0613', that is characterized by its large flowers that are deep pink in color, its floriferous blooming habit, and its long flowering season, blooming continuously from spring until the fall in Beamsville, Canada.

2 Drawing Sheets

Botanical classification: *Mandevilla* hybrid.
Cultivar designation: 'FRI0613'.

BACKGROUND OF THE INVENTION

The present invention relates to a new and distinct cultivar of *Mandevilla* plant of hybrid origin, botanically known as *Mandevilla* 'FRI0613' and will be referred to hereafter by its cultivar name, 'FRI0613'. 'FRI0613' is a new cultivar of tropical *Mandevilla* grown for use as a landscape and container plant.

The Inventor discovered 'FRI0613' in June of 2013 as a chance seedling of *Mandevilla* 'Sunparareki' (U.S. Plant Pat. No. 25,101) that was found growing in a container at his nursery in Beamsville, Ontario.

Asexual propagation of the new cultivar was first accomplished by stem cuttings in Beamsville, Ontario in July of 2013 by the Inventor. Asexual propagation by stem cuttings has determined that the characteristics of the new cultivar are stable and are reproduced true to type in successive generations.

SUMMARY OF THE INVENTION

The following traits have been repeatedly observed and represent the characteristics of 'FRI0613'. These attributes in combination distinguish 'FRI0613' as a new and distinct cultivar of *Mandevilla*.

1. 'FRI0613' exhibits large flowers that are deep pink in color with darker pink veins.
2. 'FRI0613' exhibits a floriferous blooming habit.
3. 'FRI0613' exhibits a long flowering season, blooming continuously from spring until the fall in Beamsville, Canada.

The parent of 'FRI0613', 'Sunpararekin', is similar to 'FRI0613' in having a linanous growth habit and in having a similar height and spread. 'Sunpararekin', differs from 'FRI0613' in having flowers that are deep red in color, in being less floriferous, and in having a shorter flowering season. 'FRI0613' can be most closely compared to the

*Mandevilla* cultivars 'Alice Dupont' (not patented) and 'Sunparasupre'. 'Alice Dupont' is similar to 'FRI0613' in having a long flowering season. 'Alice Dupont' differs from 'FRI0613' in having flowers that are light pink in color with a yellow throat and in being less floriferous. 'Sunparasupre' (U.S. Pat. No. 25,100). 'Sunparasupre' differs most significantly in having smaller flowers that are red in color.

BRIEF DESCRIPTION OF THE DRAWINGS

The accompanying colored photographs illustrate the overall appearance and distinct characteristics of the new *Mandevilla*. The photographs were taken of plants of 'FRI0613' about six months in age as grown in a two-gallon hanging basket in a greenhouse in Beamsville, Ontario.

The photograph in FIG. 1 provides a side view of 'FRI0613' in bloom.

Figure 1:
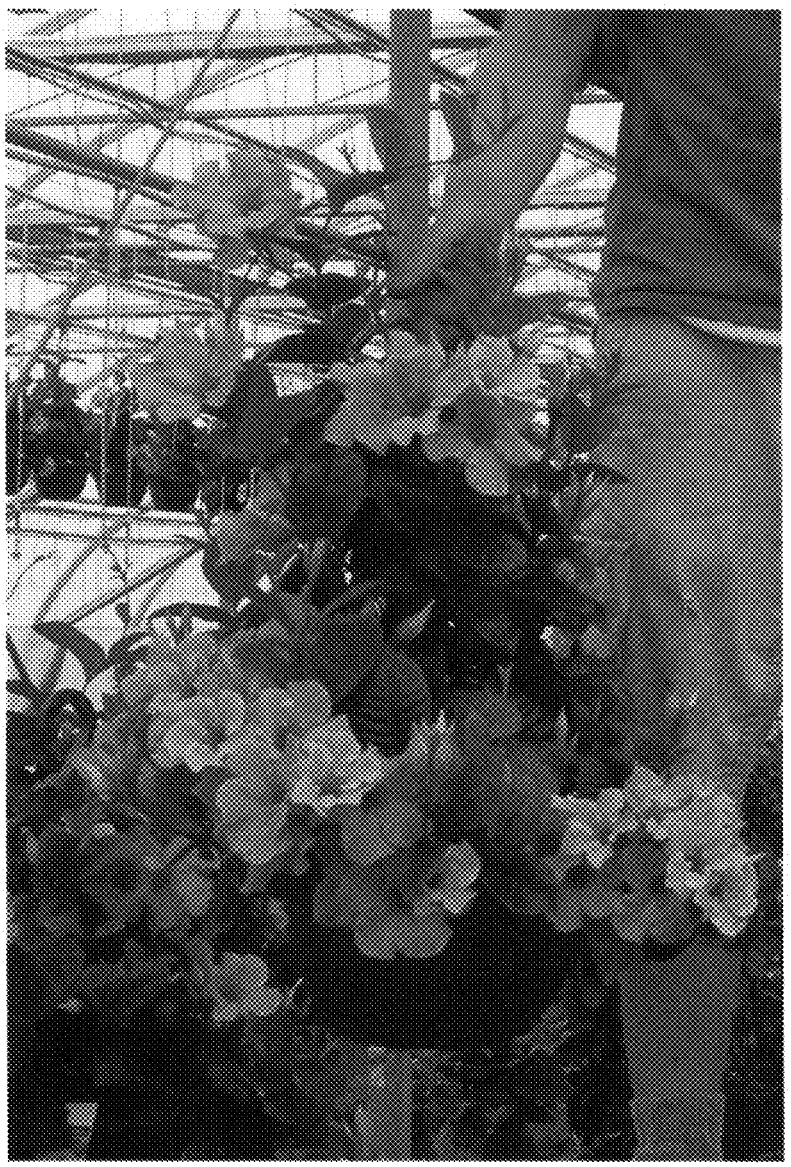
Figure 2:
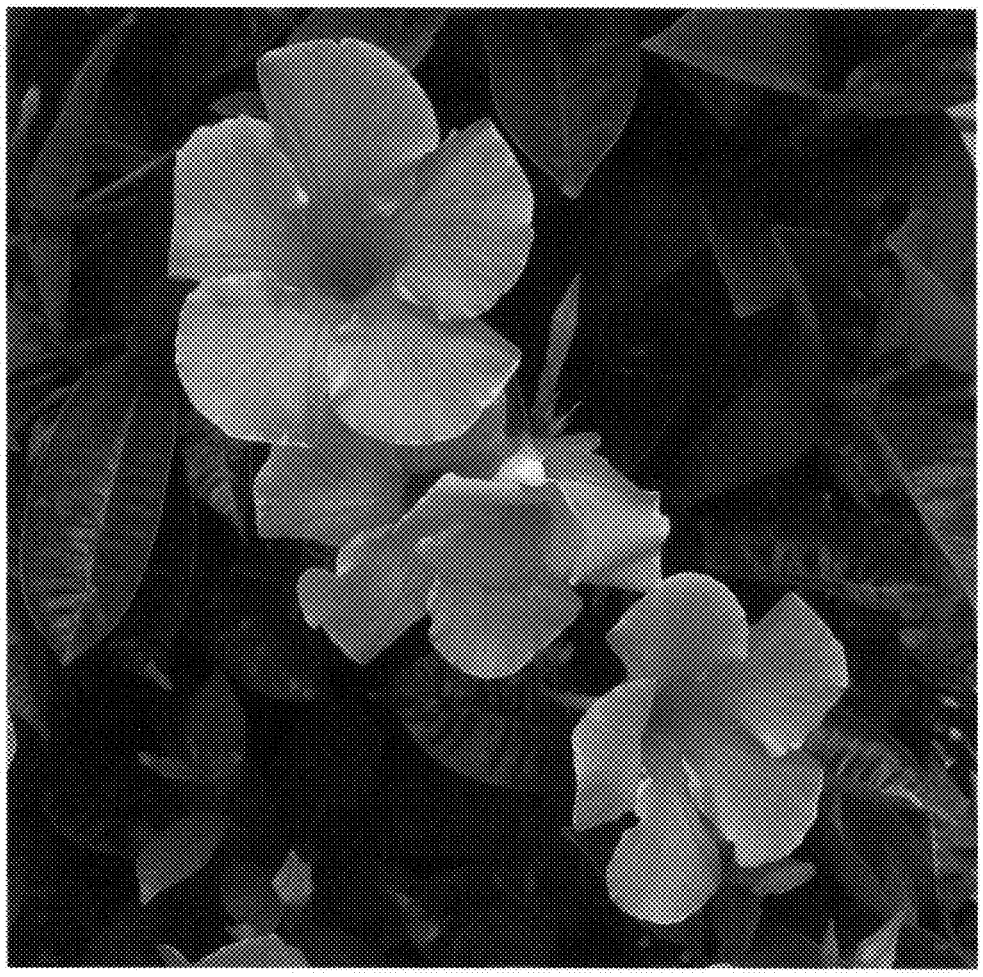

The photograph in FIG. 2 provides a close-up view of an inflorescence of 'FRI0613'.

The colors in the photographs are as close as possible with the digital photography and printing techniques utilized and the color codes in the detailed botanical description accurately describe the new *Mandevilla*.

DETAILED BOTANICAL DESCRIPTION OF THE PLANT

The following is a detailed description of 4 month-old plants of the new cultivar as grown in two-quart containers in a greenhouse in Beamsville, Ontario. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General characteristics:

*Blooming period.*—Continuously from spring until fall in Beamsville, Ontario.

*Plant type.*—Tropical evergreen vine.
*Plant habit.*—Lianous.
*Height and spread.*—Can reach a height of 3.5 to 4 m in a season growing in a container and up to 70 cm in width when on a trellis.
*Hardiness.*—At least to U.S.D.A. Zone 11, grown as a tropical.
*Diseases.*—No particular susceptibility and resistance to diseases has been observed.
*Root description.*—Fibrous and fine, root color 161D.
*Root development.*—Roots initiate in about 4 weeks and develop as a young rooted plant in about 6 weeks.
*Propagation.*—Stem cuttings.
*Growth rate.*—Vigorous.
*Branching.*—Basal branches, vining branches are unbranched.

Stem description:
*Shape.*—Round.
*Stem color.*—Young growth; a blend of 144A and 183A, mature growth; 144A and becoming suffused with 183A.
*Stem size.*—Main stems; up to 38 cm in length (at 4 months in age in a 2-qt container) and 2 mm in width, secondary basal stems; an average of 13 cm in length and 2 mm in diameter.
*Stem surface.*—Glabrous and semi-glossy.
*Stem aspect.*—Emerge nearly upright, become lianous and needing support.
*Stem strength.*—Very strong at base and becoming moderately strong as it vines.
*Branching.*—An average of 1 main stem and 1 secondary basal stems.
*Internode.*—An average of 2 cm near base and 10 cm in length towards terminus.

Foliage description:
*Leaf shape.*—Broadly elliptic.
*Leaf division.*—Simple.
*Leaf base.*—Cordate.
*Leaf apex.*—Mucronate.
*Leaf venation.*—Pinnate, upper surface; N144A, lower surface; veins match leaf color with midrib 144D.
*Leaf margins.*—Entire.
*Leaf attachment.*—Petiolate.
*Leaf arrangement.*—Opposite.
*Leaf orientation.*—Held horizontal.
*Leaf aspect.*—Slightly upward on both sides of mid vein.
*Leaf surface.*—Upper surface highly glossy, lower surface semi-glossy.
*Leaf color.*—Young leaves upper and lower surface; a blend of 144A and 146A, mature leaves upper surface; N137A with slight under tones of 144A; mature leaves lower surface; 144A.
*Leaf substance.*—Thick and coriaceous.
*Leaf size.*—An average of 9.5 cm in length and 5.5 cm in width.
*Leaf quantity.*—An average of 6 leaves per stem 9 cm in length at base and an average of 14 leaves on the total length of stem 38 cm in length.
*Petioles.*—An average of 1 cm in length and 4 mm in diameter, 144A in color, pubescent and glossy surface, upper surface is sulcate.

Flower description:
*Inflorescence type.*—Flowers are arranged in racemes of an average of 6 flowers that open individually.
*Inflorescence size.*—An average of 16 cm in width and 9 cm in depth on a raceme with 2 flowers open.
*Lastingness of flowers.*—About 6 days, self cleaning.
*Flower size.*—An average of 7.5 cm in depth and 9 cm in diameter.
*Flower fragrance.*—None detected.
*Flower type.*—Funnel-formed-tubular with free lobes spreading.
*Flower number.*—An average of 6 flowers per inflorescence and one inflorescence per stem at 4 months in age, continuously produces blooms.
*Flower aspect.*—Held at an average angle of 45° from peduncle.
*Flower bud.*—Elliptic in shape, an average of 6.5 cm in length and 2 cm in width, young bud color; mostly 157A with overlays of 185C and 185D at the bud petal base and margins, mature bud color; base is a blend of 63A, 185D and 155A, center 155A blending at the apex with 63D.
*Flower attachment.*—Pedicellate.
*Petals.*—5, lower ⅔ fused at base into tube, free lobes; an average of 4 cm in length and 3.5 cm in width, irregular and asymmetrical in shape with one side rounded and the other side lanceolate-like, apex rounded, margins undulate, color upper surface when opening and mature; a blend of 68A, 68B, 68C, with veins 63B, color lower surface when opening and mature, a blend of 68B, 68C and N155C on rounded side and a blend of 68A, and 63A on lanceolate-shape side, glabrous on upper surfaces and satiny on lower surface, tube; 4.5 cm in length and 2 cm at width at junction with lobes and 5 mm in width at base, surface in satiny on outer surface and velvety on inner surfaces, color outer surface; a blend of 63A, 68B and 60C and 145D at base, color inner surface; 46B with streaks of 35A and 17B.
*Calyx.*—Campanulate, an average of 7 mm in length and 4 mm in width.
*Sepals.*—5, lower 50% fused, both surfaces glossy and 144A in color, free tips; held upright, an average of 4 mm in length and 1.5 mm in width, 144A to 144B in color with very tips 145C and with age becomes suffused with 178C, lanceolate in shape, acuminate apex, entire margin.
*Peduncles.*—An average of 3.5 cm in length and 4 mm in diameter, strong, 144A in color; smooth and glossy surface.
*Pedicels.*—Up to 1 cm in length and 3 mm in width, moderately strong, 144A in color, smooth and glossy surface.

Reproductive organs:
*Gynoecium.*—1 pistil, about 2 cm in length, stigmas; conical in shape, 1.5 mm in diameter and 145A in color, style; 1.8 cm in length and 157A in color, ovary; conical in shape, 2 mm in length and width, and 144A in color.
*Androecium.*—5 stamens; anthers; basifixed, linear in shape, an average of 7 mm in length and 1.5 mm in diameter, 13A in color with base pubescent, filament; adnate to base of tube, an average of 1.5 cm in length and 2 mm in width, and 145C in color, pollen; sparse in quantity and 4D in color.
*Fruit/seeds.*—None observed to date.

It is claimed:

1. A new and distinct cultivar of *Mandevilla* plant named 'FRI0613' as herein illustrated and described.

* * * * *